(12) United States Patent
Guo et al.

(10) Patent No.: US 10,960,180 B2
(45) Date of Patent: *Mar. 30, 2021

(54) CATHETER SHAFT AND METHOD OF ITS MANUFACTURE

(71) Applicant: St. Jude Medical, Atrial Fibrillation Division, Inc., St. Paul, MN (US)

(72) Inventors: Xiaoping Guo, Eden Prairie, MN (US); Richard E. Stehr, Tuscon, AZ (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 321 days.

This patent is subject to a terminal disclaimer.

(21) Appl. No.: 15/963,813

(22) Filed: Apr. 26, 2018

(65) Prior Publication Data

US 2018/0243531 A1    Aug. 30, 2018

Related U.S. Application Data

(60) Continuation of application No. 15/140,750, filed on Apr. 28, 2016, now Pat. No. 9,987,463, which is a (Continued)

(51) Int. Cl.
*A61M 25/00* (2006.01)
*B29C 48/151* (2019.01)
(Continued)

(52) U.S. Cl.
CPC ...... *A61M 25/005* (2013.01); *A61M 25/0009* (2013.01); *A61M 25/0012* (2013.01); (Continued)

(58) Field of Classification Search
CPC . B29C 48/151; B29C 61/006; B29C 63/0069; B29D 23/001; A61M 2025/0059; B29L 2031/7542
(Continued)

(56) References Cited

U.S. PATENT DOCUMENTS 4,776,334 A    10/1988  Prionas
4,934,049 A     6/1990  Kiekhafer et al.
(Continued)

FOREIGN PATENT DOCUMENTS

WO    2007136981    11/2007

OTHER PUBLICATIONS

PEBAX Mechanical Properties Data Sheet, 8 pages, 2015, used as evidentiary reference. (Year: 2015).*

(Continued)

*Primary Examiner* — Joseph S Del Sole
*Assistant Examiner* — Lawrence D. Hohenbrink, Jr.
(74) *Attorney, Agent, or Firm* — Wiley Rein LLP

(57) ABSTRACT

A method of manufacturing a catheter shaft includes the steps of forming an inner layer of a first polymeric material, forming a plait matrix layer including a second polymeric material about the inner layer, and forming an outer layer of a third polymeric material about the plait matrix layer. The plait matrix layer includes a braided wire mesh partially or fully embedded within the second polymeric material, which is different from at least one of the first polymeric material forming the inner layer and the third polymeric material forming the outer layer. The second polymeric material has a higher yield strain and/or a lower hardness than at least the first polymeric material, and preferably both the first and the third polymeric materials. The first polymeric material and the third polymeric material may be different or the same. The catheter shaft may be formed by stepwise extrusion, co-extrusion, and/or reflow processes.

8 Claims, 3 Drawing Sheets

Related U.S. Application Data continuation of application No. 13/795,647, filed on Mar. 12, 2013, now Pat. No. 9,352,116, which is a division of application No. 11/967,220, filed on Dec. 30, 2007, now Pat. No. 8,431,057.

(51) Int. Cl.
  *B29C 61/00* (2006.01)
  *B29D 23/00* (2006.01)
  *A61M 25/01* (2006.01)
  *B29C 63/00* (2006.01)
  *B29L 31/00* (2006.01)
  *B29K 27/18* (2006.01)
  *B29K 105/16* (2006.01)

(52) U.S. Cl.
  CPC .... *A61M 25/0043* (2013.01); *A61M 25/0108* (2013.01); *B29C 48/151* (2019.02); *B29C 61/006* (2013.01); *B29C 63/0069* (2013.01); *B29D 23/001* (2013.01); *A61M 25/0045* (2013.01); *A61M 2025/0059* (2013.01); *A61M 2205/32* (2013.01); *B29K 2027/18* (2013.01); *B29K 2105/16* (2013.01); *B29L 2031/7542* (2013.01)

(58) Field of Classification Search
  USPC ................. 264/209.1, 241, 171.27; 156/149; 604/527
  See application file for complete search history.

(56) References Cited

U.S. PATENT DOCUMENTS

| | | | |
|---|---|---|---|
| 5,147,315 A | | 9/1992 | Weber |
| 5,248,305 A | | 9/1993 | Zdrahala |
| 5,368,564 A | | 11/1994 | Savage |
| 5,395,328 A | | 3/1995 | Ockuly et al. |
| 5,478,330 A | * | 12/1995 | Imran .............. A61B 18/1492 604/525 |
| 5,782,900 A | | 7/1998 | de la Rama et al. |
| 5,836,946 A | | 11/1998 | Diaz et al. |
| 5,851,464 A | | 12/1998 | Duvaila et al. |
| 5,879,499 A | | 3/1999 | Corvi |
| 5,891,112 A | | 4/1999 | Samson |
| 5,906,605 A | * | 5/1999 | Coxum ............... A61M 25/005 600/373 |
| 5,971,975 A | | 10/1999 | Mills et al. |
| 6,001,095 A | | 12/1999 | de la Rama et al. |
| 6,106,510 A | | 8/2000 | Lunn et al. |
| 6,235,021 B1 | | 5/2001 | Sieben |
| 6,273,880 B1 | | 8/2001 | Berg et al. |
| 6,783,521 B2 | | 8/2004 | Ponzi et al. |
| 7,229,437 B2 | | 6/2007 | Johnson et al. |
| 7,234,225 B2 | | 6/2007 | Johnson et al. |
| 2004/0143256 A1 | | 7/2004 | Bednarek |
| 2004/0193140 A1 | | 9/2004 | Griffin et al. |
| 2006/0095050 A1 | | 5/2006 | Hartley et al. |
| 2006/0100602 A1 | | 5/2006 | Klint |
| 2006/0151923 A1 | * | 7/2006 | Wilkowske ....... A61M 25/0012 264/500 |
| 2007/0265658 A1 | | 11/2007 | Nelson et al. |
| 2007/0299424 A1 | | 12/2007 | Cumming et al. |
| 2008/0161762 A1 | | 7/2008 | Stehr et al. |

OTHER PUBLICATIONS

International Search Report and Written Opinion for PCT/US08/85185, dated Jan. 29, 2009.

International Search Report and Written Opinion for PCT/US08/84560, dated Jan. 28, 2009.

International Search Report and Written Opinion for PCT/US08/845560, dated Jan. 28, 2009.

Pebax Mechanical Properties Data Sheet, Mar. 2011, www.pebax.com.

Arkema, "Pebax Mechanical Properties," Pebax Polyether Block Amides 2006.

PEBAX Mechanical Data Property Sheet, downloaded Jul. 15, 2015, Pebax.com.

* cited by examiner

CATHETER SHAFT AND METHOD OF ITS MANUFACTURE

CROSS-REFERENCE TO RELATED APPLICATIONS

This application is a continuation of U.S. application Ser. No. 15/140,750, filed 28 Apr. 2016, now ("the '750 application"), which is a continuation of U.S. application Ser. No. 13/795,647, filed 12 Mar. 2013, now U.S. Pat. No. 9,352,116 ("the '647 application"), which is a divisional of U.S. application Ser. No. 11/967,220, filed 30 Dec. 2012, now U.S. Pat. No. 8,431,057 ("the '220 application"). This application is also related to U.S. application Ser. No. 11/967,219, filed 30 Dec. 2007 ("the '219 application"). The '750, '647, '219, and '220 applications are hereby incorporated by reference as though fully set forth herein.

BACKGROUND

The instant invention relates to catheters that are used in the human body. In particular, the instant invention relates to catheters using a hyperelastic plait matrix to improve the kink resistance and maneuverability of the catheter.

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

Since the path through the patient's vasculature to the intended site is often long and tortuous, steering forces typically must be transmitted over relatively great distances. Accordingly, it is desirable for a catheter to have sufficient axial (e.g., column) strength to be pushed through the patient's vasculature via a force applied at its proximal end ("pushability"). It is also desirable for a catheter to transmit a torque applied at the proximal end to the distal end ("torqueability"). Pushability and torqueability (collectively, "maneuverability") permit a physician to manipulate a catheter to an intended site and then properly orient the catheter. It is also desirable for a catheter to have sufficient flexibility to substantially conform to the patient's vasculature and yet resist kinking as it does so. Kinking is often the result of a localized failure of the material of the catheter when localized stresses exceed the yield strength of the material.

To provide pushability, torqueability, flexibility, and kink resistance, many extant catheters are made of engineering polymer materials reinforced with metallic wire braiding plaits. The characteristics of pushability, torqueability, flexibility, and kink resistance are often in tension with one another, however, with improvements in one requiring compromises in others.

BRIEF SUMMARY

It is desirable to provide a catheter with improved flexibility, kink resistance, and maneuverability.

It is also desirable to provide a catheter with improved mechanical integrity.

In a first aspect, the present invention provides a method of manufacturing a catheter shaft, generally including the following steps: forming an inner layer of a first melt-processable polymer; forming a plait matrix layer about the inner layer, the plait matrix layer including a braided wire mesh embedded (e.g., partially or fully embedded) in a matrix material layer including a second melt-processable polymer; and forming an outer layer of a third melt-processable polymer about the plait matrix layer, wherein the second melt-processable polymer forming the matrix material layer is different from at least one of the first melt-processable polymer and the third melt-processable polymer. Optionally, the braided wire mesh may be coated with silicone.

Typically, the matrix material (e.g., the second melt-processable polymer) will be hyperelastic relative to at least the first melt-processable polymer, and will preferably be hyperelastic relative to both the first melt-processable polymer and the third melt-processable polymer (for example, where the first and second melt-processable polymers are the same). The yield strain of the matrix material is preferably between about 3% and about 100%, and more preferably between about 5% and about 50%. Suitable materials for the matrix material include styrenic block copolymers (e.g., Kraton®), functionalized thermoplastic olefins, thermoplastic elastomeric alloys, thermoplastic polyurethanes (e.g., Estane®, Pellethane®), polyamide-based thermoplastic elastomers (e.g., Pebax®), polyester-based thermoplastic elastomers (e.g. Hytrel®), ionomeric thermoplastic elastomers (e.g., Surlyn®), and any combinations thereof. The Shore hardness of the matrix material may be between about 10D and about 85D, more preferably between about 20D and about 70D.

In some aspects of the invention, the plait matrix layer is formed about the inner layer by braiding the wire mesh about the inner layer to form a reinforced inner layer and then extruding the matrix material about the reinforced inner layer to form the plait matrix layer. Similarly, the outer layer may be formed about the plait matrix layer by extruding the third material to form the outer layer about the plait matrix layer. It is also contemplated that the matrix material and the third material may be co-extruded to concurrently form the plait matrix layer and the outer layer.

In other aspects of the invention, the inner layer, the plait matrix layer, and the outer layer are heated to bond the inner layer, the plait matrix layer, and the outer layer together, thereby forming a unitary catheter shaft. A heat-shrink tube may be introduced about the outer layer prior to the heating step.

Also disclosed herein is a method of forming a catheter shaft, including the steps of: forming an inner layer of a first material; and forming a plait matrix layer about the inner layer, the plait matrix layer including a braided wire mesh at least partially embedded within a second material, wherein the second material is hyperelastic relative to the first material. An outer layer of a third material may optionally be formed about the plait matrix layer. At least one of the first material and the second material may include a radiopaque filler material.

The step of forming a plait matrix layer will typically include forming the braided wire mesh about the inner layer; and impregnating the braided wire mesh with the second material. The braided wire mesh may be formed about the inner layer by braiding the wire mesh about the inner layer or by braiding the wire mesh about a core, decoring the braided wire mesh, and placing the braided wire mesh about the inner layer. Similarly, the braided wire mesh may be impregnated with the second material by forming a layer of the second material about the braided wire mesh and heating the layer of the second material to flow and impregnate the braided wire mesh or by extruding a layer of the second material about the braided wire mesh.

In another aspect, the present invention provides a catheter shaft formed according to a method including the steps of: forming an inner layer of a first melt-processable polymer; forming a plait matrix layer about the inner layer, the plait matrix layer including a braided wire mesh embedded in a matrix material layer of a second melt-processable polymer; and forming an outer layer of a third melt-processable polymer about the plait matrix layer, wherein the matrix material is hyperelastic relative to at least one of the first melt-processable polymer and the third melt-processable polymer.

In still another aspect of the present invention, a catheter shaft includes: an inner layer of a first polymeric material; and a plait matrix layer bonded to the inner layer, the plait matrix layer including a braided wire mesh embedded in a second polymeric material, wherein the second polymeric material is hyperelastic relative to the first polymeric material. The catheter shaft may also include an outer layer of a third polymeric material bonded to the plait matrix layer. The third polymeric material forming the outer layer is optionally the same as the first polymeric material forming the inner layer.

In still another aspect of the present invention, a catheter shaft includes: an inner layer of a first polymeric material; a plait matrix layer bonded to the inner layer, the plait matrix layer including a braided wire mesh embedded in a second polymeric material; and an outer layer of a third polymeric material. The second polymeric material is hyperelastic relative to both the first polymeric material and the second polymeric material.

In still another aspect of the present invention, a catheter shaft includes: an inner layer of a first polymeric material; a plait matrix layer bonded to the inner layer, the plait matrix layer including a braided wire mesh embedded in a second polymeric material; and an outer layer of a third polymeric material. The first material forming the inner layer and the third material forming the outer layer are selected to have sufficiently high mechanical strength and rigidity for shaft maneuverability. The first material and the third material may be different materials or the same material, and are typically selected from the group consisting of thermoplastics, including polyesters, polyamides, polycarbonate, polysulfones, polyimides, polyketones, liquid crystal polymers, functionalized polypropylene and copolymers or any combinations of the above, or high performance engineering thermoplastic elastomers with a durometer of at least about 60D, including polyester-based thermoplastic elastomers, polyamide-based thermoplastic elastomers, thermoplastic polyurethanes, and the like.

An advantage of the present invention is that it provides a catheter having increased flexibility and kink resistance.

Another advantage of the present invention is that it enhances mechanical integrity of the catheter with increased torqueability and column strength, as well as pushability.

The foregoing and other aspects, features, details, utilities, and advantages of the present invention will be apparent from reading the following description and claims, and from reviewing the accompanying drawings.

DETAILED DESCRIPTION

The present invention provides a catheter shaft suitable for use in the human vasculature for known medical procedures, such as cardiac mapping and ablation. Catheters utilizing catheter shafts according to the present invention advantageously exhibit improved maneuverability, flexibility, and kink resistance. For purposes of this description, the invention will be described in connection with an elongate electrophysiology catheter. It is contemplated, however, that the described features and methods may be incorporated into any number of catheters (e.g., steerable catheters, introducer catheters, and the like) as would be appreciated by one of ordinary skill in the art.

Figure 1:
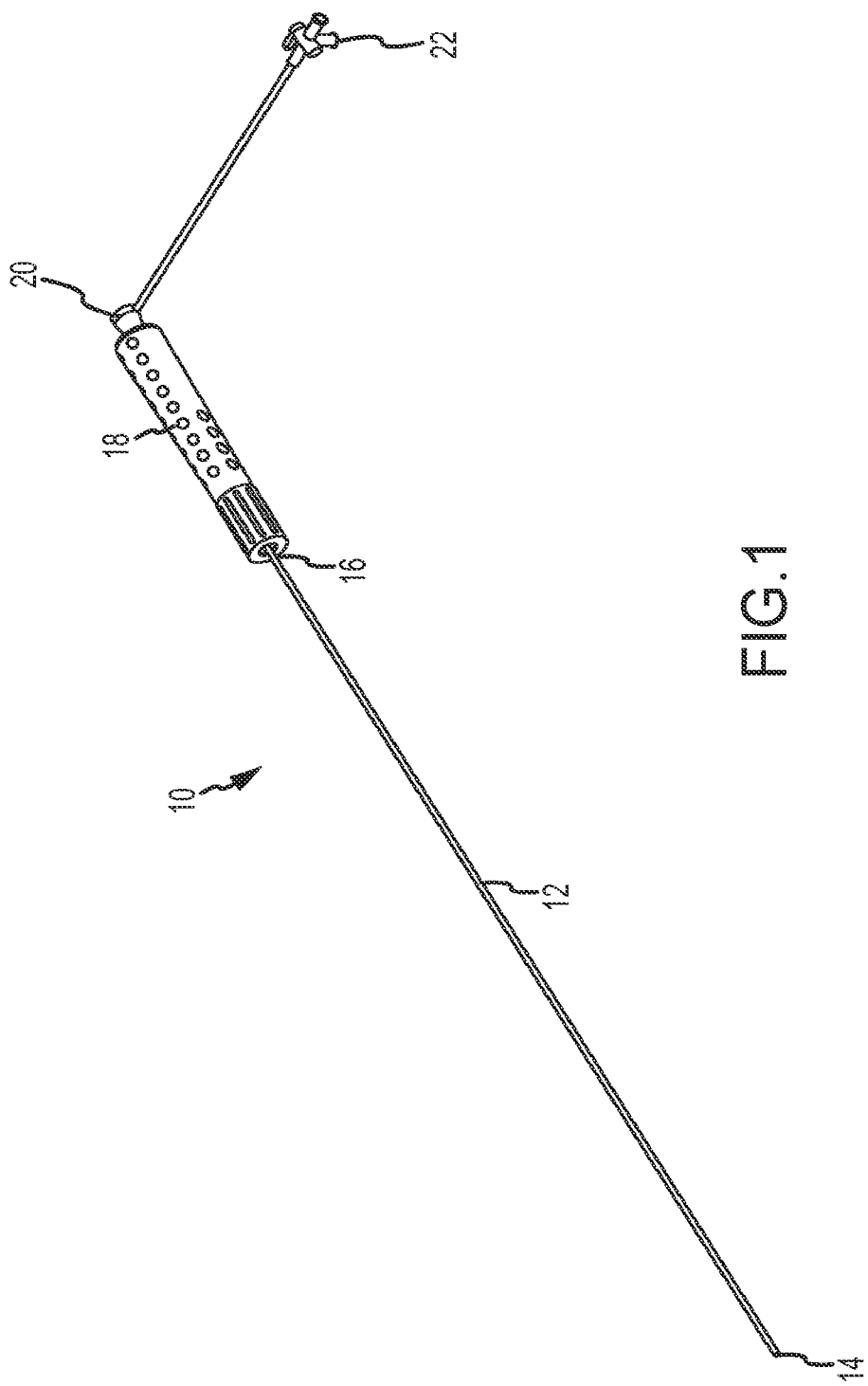
FIG. 1 is a perspective view of an exemplary catheter according to an embodiment of the present invention.

Referring now to the figures, and in particular to FIG. 1, an electrophysiology catheter 10 includes a shaft 12 having a distal end 14 and a proximal end 16. A handle 18 may be coupled to proximal end 16 of shaft 12 to control catheter 10 (e.g., to push and/or torque catheter 10). Catheter 10 may also include a hub 20 operably coupled to an inner lumen (not shown) within handle 18. A valve 22 may be operably connected to hub 20. Of course, it is also contemplated that any known device for manipulation of catheter 10 may be coupled to proximal end 16 thereof, including, without limitation, robotic manipulation devices and the like.

The basic method of manufacture of catheter 10, and in particular of at least a portion of shaft 12, according to an embodiment of the present invention will be described with reference to FIGS. 2-5. As they are assembled, the catheter components will be collectively referred to as a "catheter shaft assembly."

Figure 2:
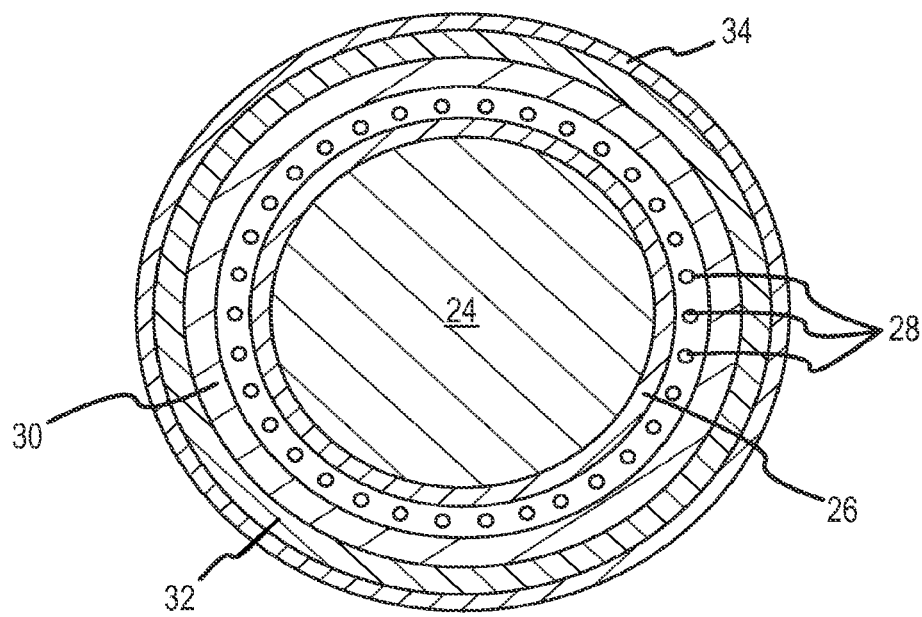
FIG. 2 is an axial cross-sectional view of the various components of a catheter shaft assembly according to an embodiment of the present invention prior to the application of energy to melt process the catheter shaft assembly.

As depicted in FIG. 2, a mandrel or hypotube 24, which is preferably round in cross-section and preferably from about 6 inches to about 4 feet in length, is a component of the catheter shaft assembly, and may be the first component thereof during manufacture of catheter shaft 12. Typically, mandrel 24 is disposable. Mandrel 24 has a distal end and a proximal end. An inner layer 26 is formed about mandrel 24. For example, inner layer 26 may be knotted at one end (e.g., the distal end) and then fed onto mandrel 24.

Inner layer 26 may be an extruded polymeric tubing, such as pre-extruded (and optionally chemically-etched) polytetrafluoroethylene (PTFE) tubing (e.g., Teflon® brand tubing). Inner layer 26 may also be made of other melt-processable polymers, including, without limitation, fluorinated ethylene-propylene copolymer (FEP), perfluoroalkoxyethylene (PFA), poly(vinylidene fluoride), poly(ethylene-co-tetrafluoroethylene), and other fluoropolymers with surface treatment such as chemical etching, plasma and corona treatment, and the like. One of ordinary skill will also appreciate that the inner layer 26 may be made of some melt-processable thermoplastic elastomeric polymers with sufficiently high mechanical strength and rigidity (e.g., durometer of at least about 60D), including, without limitation, polyamide-based thermoplastic elastomers (namely poly(ether-block-amide), Pebax®), polyester-based thermoplastic elastomers (e.g., Hytrel®), thermoplastic polyurethanes (e.g., Pellethane®, Estane®), ionic thermoplastic elastomers, functionalized thermoplastic olefins and any combinations thereof. In general, suitable materials for inner layer 26 may also be selected from various thermoplastics, including, without limitation, polyamides, polyurethanes, polyesters, functionalized polyolefins, polycarbonate, polysulfones, polyimides, polyketones, liquid crystal polymers and any combination thereof. Specific suitable materials for inner layer 26 include, without limitation, Pebax® 7233, Pebax® 6333, Grilamid L25, Rilsan AESNO, Rilsan BESNO, Makrolon 3108, Makrolon 1239, and the like.

A plait matrix layer including a braided wire mesh assembly 28 and a second polymeric material layer 30 (also referred to herein as "matrix material layer 30," and the polymeric material therein as "matrix material") may then be formed about inner layer 26. Braided wire mesh assembly 28 may be formed of stainless steel wire, including, for example, 0.003" high tensile stainless steel wire. Braided wire mesh assembly 28 may be formed in a standard braid pattern and density, for example, about 16 wires at about 45 to about 60 picks per inch ("PPI") density. Alternatively, a braid may be used that is characterized by a varying braid density. For example, braided wire mesh assembly 28 may be characterized by a first braid density at proximal end 16 of catheter shaft 12 and then transition to one or more different braid densities as braided wire mesh assembly 28 approaches distal end 14 of catheter shaft 12. The braid density at distal end 14 may be greater or less than the braid density at proximal end 16. In a specific example, the braid density at proximal end 16 is about 50 PPI and the braid density at distal end 14 is about 10 PPI. In another embodiment, the braid density at distal end 14 is about 20% to about 35% of the braid density at proximal end 16.

Braided wire mesh assembly 28 may be formed separately on a disposable core and slipped about inner layer 26. Alternatively, braided wire mesh assembly 28 may be braided directly upon inner layer 26 to form a reinforced inner layer. In addition, one or more portions of braided wire mesh assembly 28 may be heat tempered and cooled before incorporation into the catheter shaft assembly through methods that are known to those of ordinary skill in the art. The action of heat tempering may help to release the stress on the wire and help reduce radial forces.

Matrix material layer 30 may then be formed about braided wire mesh assembly 28. In some embodiments of the invention, matrix material layer 30 is extruded about the reinforced inner layer (that is, about braided wire mesh assembly 28) to form the plait matrix layer. In other embodiments of the invention, matrix material layer 30 is separately extruded and then slipped about braided wire mesh assembly 28 as part of the catheter shaft assembly.

Preferably, matrix material layer 30 will be of a different material than inner layer 26. In particular, in some embodiments of the invention, matrix material 30 will be hyperelastic relative to inner layer 26. That is, matrix material layer 30 (and therefore the plait matrix layer, as described in further detail below) may have a lower flexural modulus and a higher yield strain than inner layer 26. The lower flexural modulus and higher yield strain of matrix material layer 30 relative to inner layer 26 advantageously promotes maneuverability and kink resistance of catheter shaft 12. Typically, the yield strain of matrix material layer 30 will be between about 3% and about 100%, and more preferably between about 5% and about 50%.

Suitable materials for matrix material layer 30 may be selected from various thermoplastic elastomer resins, including, without limitation, styrenic block copolymers (e.g., Kraton D (including styrene-butadiene-styrene (SBS) triblock copolymers and styrene-isoprene-styrene (SIS) triblock copolymers); Kraton G (including styrene-ethylene/butylene-styrene copolymers and styrene-ethylene/propylene-styrene (SEPS) copolymers; and SIBStar styre-isobutylene-styrene triblock copolymers), thermoplastic olefins (TPO) and elastomeric alloys (e.g., Santoprene and Versaflex), thermoplastic polyurethanes (e.g., Pellethane; Estane; Tecoflex; Tecothane; Carbothane; Tecoplast; and Tecophilic TPUs), poly(ether-b-amide)s (e.g., Pebax®; Vestamid® E; and Grilamide® ELY), poly(ether-ester)s (e.g., Hytrel), ionomeric thermoplastic elastomers (e.g., Surlyn), and any combinations thereof. Particularly suitable materials for matrix material layer 30 include, without limitation, Pebax® 4033, Pebax® 5033, Pellethane 2363-55D, and Surlyn 9320.

In some embodiments of the invention, matrix material layer 30 forms the outermost layer of catheter shaft 12. Alternatively, an outer layer 32 may be formed about the plait matrix layer (that is, about matrix material layer 30). Outer layer 32 may be formed by extruding a third polymer material about the matrix material layer 30. In some embodiments of the invention, outer layer 32 and matrix material layer 30 are co-extruded about braided wire mesh assembly 28. In other embodiments of the invention, outer layer 32 may be separately extruded and then slipped about matrix material layer 30, such as illustrated in FIG. 2.

Outer layer 32 is typically a melt-processable polymeric tube, such as an extruded polytetrafluoroethylene (PTFE) tubing (e.g., Teflon® brand tubing), optionally with surface chemical etching. One of ordinary skill will appreciate that outer layer 32 may also be made of other melt-processable fluoropolymers, including, without limitation, fluorinated ethylene-propylene copolymer (FEP), perfluoroalkoxyethylene (PFA), poly(vinylidene fluoride), poly(ethylene-co-tetrafluoroethylene), and the like with surface treatment. Outer layer 32 may also be made of melt processable thermoplastic elastomers with sufficiently high mechanical strength and rigidity, including, without limitation, polyamide-based thermoplastic elastomers (namely poly(ether-block-amide), Pebax®), polyester-based thermoplastic elastomers (e.g., Hytrel®), thermoplastic polyurethanes (e.g., Pellethane®, Estane®), and the like, and any combinations thereof. In general, outer layer 32 may also be made of thermoplastics selected from the group consisting of polyamides, polyurethanes, polyesters, functionalized polyolefins, polycarbonate, polysulfones, polyketones, liquid crystal polymers, functionalized polyolefins, and any combination thereof. Specific suitable materials for outer layer 32 include, without limitation, Pebax® 7233 and Pebax® 6333, Grilamid L25, Rilsan AESNO, Rilsan BESNO, Makrolon 3108, and the like. One of ordinary skill in the art will readily appreciate that the third material of outer layer 32 may be different from or substantially identical to the first material of inner layer 26 as desired, and will further appreciate how to select suitable materials for inner layer 26 and outer layer 32 for a particular application of catheter 10.

Typically, matrix material layer 30 will be different from at least one of the first material forming the inner layer 26 and the third material forming the outer layer 32. Matrix material layer 30 is preferably hyperelastic relative to either inner layer 26 or outer layer 32, and, in some embodiments, matrix material layer 30 is hyperelastic as compared to both inner layer 26 and outer layer 32.

It is desirable for there to be at least partial chemical compatibility between matrix material layer 30 and inner layer 26 and outer layer 32. This will promote inter-layer bonding between the layers of the catheter shaft assembly and reduce the likelihood of strain-induced polymer delamination under manipulation of catheter 10. Such compatibility may be provided by forming inner layer 26 and outer layer 32 of materials whose polarity and/or solubility parameter are similar to that of matrix material layer 30. Alternatively, or additionally, chemical modifications may be undertaken to achieve at least partial chemical compatibility between layers (e.g., blending and compounding matrix material layer 30 with a minor amount of the material of inner layer 26 or outer layer 32). Alternatively, surface modifications on one or more of the layers can also promote inter-layer bonding.

In some embodiments of the invention, it is desirable for the catheter shaft assembly to be radiopaque. Thus, it is contemplated that one or more of inner layer 26 and outer layer 32 may include a radiopaque filler. Suitable radiopaque fillers include, without limitation, barium sulfate, bismuth subcarbonate, bismuth trioxides, bismuth oxychloride, tungsten, tantalum, platinum, gold, and any combinations thereof. Radiopaque nanoclays may also be employed. Typically, matrix material 30 will not include such radiopaque fillers, but doing so is not outside of the spirit and scope of the present invention. As an alternative to the use of radiopaque fillers, or in addition to the use of radiopaque fillers, a radiopaque marker (not shown) may be included in the catheter shaft assembly.

Figure 3:
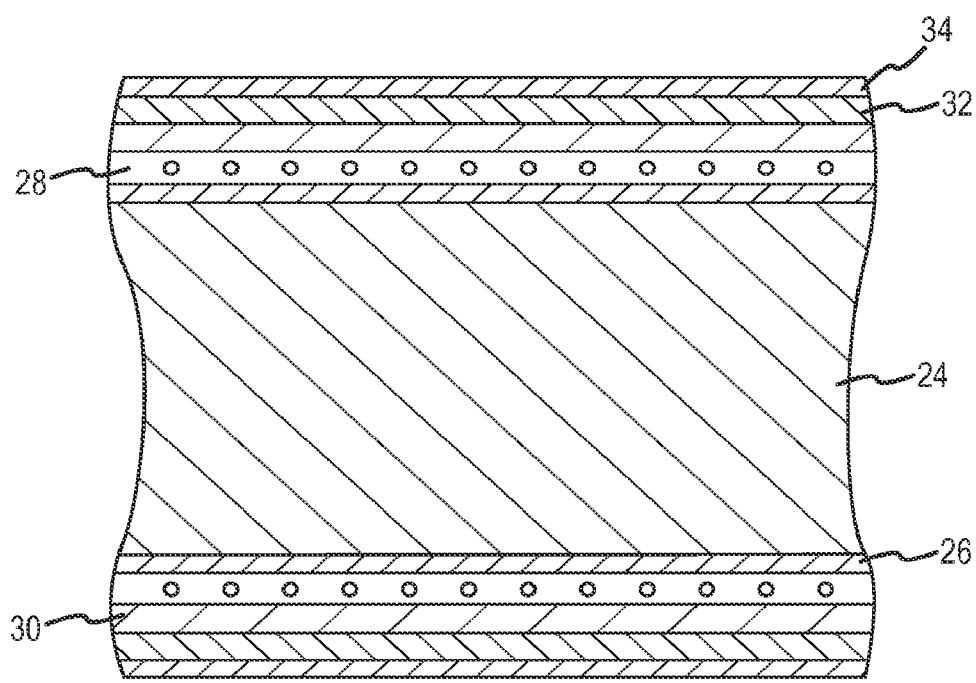
FIG. 3 is a longitudinal cross-sectional view of the various components of a catheter shaft assembly according to an embodiment of the present invention prior to the application of energy to melt process the catheter shaft assembly.

FIG. 2 displays an axial-cross section of the catheter shaft assembly including mandrel 24, inner layer 26, braided mesh assembly 28, matrix material layer 30, and outer layer 32 before thermal lamination of the various layers by heating (e.g., reflow bonding). FIG. 3 depicts a longitudinal cross-section of the catheter shaft assembly at the same stage of manufacture. In some embodiments of the invention, a layer of heat shrink 34 is placed over outer layer 32 as depicted in FIGS. 2 and 3. Heat shrink 34 is preferably a fluoropolymer such as fluorinated ethylene-propylene copolymer (FEP). As an alternative to heat shrink tube 34, the catheter shaft assembly may be placed into a suitable mold prior to subsequent processing. Either heat shrink tube 34 or a suitable mold may be generally referred to as a "shape retention structure," so named because it retains the overall shape of the catheter shaft assembly (that is, the generally circular axial cross-section) during melt-processing.

Figure 4:
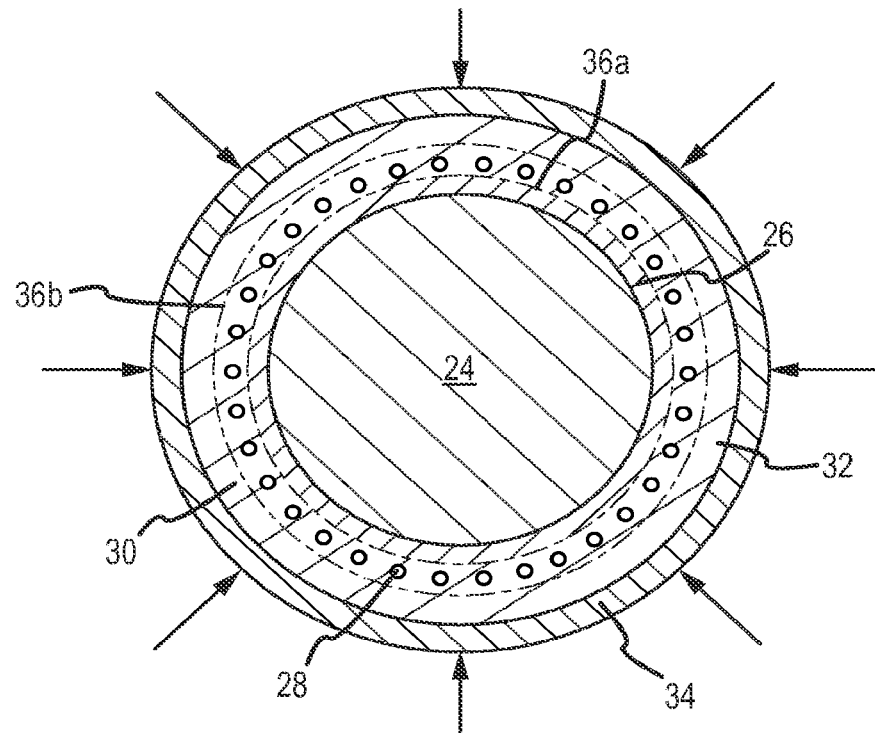
FIG. 4 is an axial cross-sectional view of a catheter shaft assembly according to an embodiment of the invention during the application of energy to melt process the catheter shaft assembly.

As shown in FIG. 4, the catheter shaft assembly may then be melt-processed. Energy (e.g., radiofrequency energy or thermal energy) is applied to the catheter shaft assembly, for example to the outer surface of the catheter shaft assembly, to bond inner layer 26, matrix material layer 30, and outer layer 32 (if present) together in a process often referred to as "reflow bonding." Heat shrink tube 34 has a higher melting or softening temperature than inner layer 26, matrix material layer 30, and outer layer 32, such that, during the melting process, heat shrink tube 34 will maintain its tubular shape and/or contract during the reflow process. The combination of applied energy and pressure exerted by heat shrink tube 34 forces melted inner layer 26, matrix material layer 30, and outer layer 32 to flow locally and redistribute about the circumference of the catheter shaft assembly and melt together, as represented by interphase lines 36a (between inner layer 26 and matrix material layer 30) and 36b (between outer layer 32 and matrix material layer 30).

Once the catheter shaft assembly has cooled, mandrel 24 can be removed, leaving a central lumen 38 (FIG. 5) extending through at least a portion of catheter shaft 12. Optionally, heat shrink tube 34 may also be removed, such that outer layer 32 becomes the outermost layer of the catheter shaft assembly.

Figure 5:
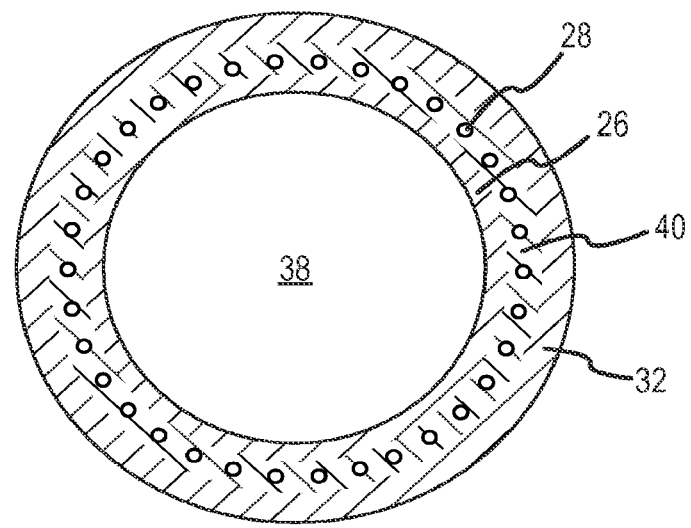
FIG. 5 is an axial cross-sectional view of a catheter shaft according to an embodiment of the invention after the application of energy to melt process the catheter shaft assembly into the catheter shaft.

FIG. 5 depicts the catheter shaft assembly after the conclusion of the reflow bonding process (that is, FIG. 5 depicts an axial-cross section of a catheter shaft formed according to an embodiment of the present invention). One of skill in the art will appreciate that, as a result of the reflow bonding process described above, matrix material layer 30 will flow and impregnate braided mesh assembly 28, such that braided mesh assembly 28 will be at least partially embedded within matrix material layer 30. In the preferred embodiments of the invention, braided mesh assembly 28 will be fully embedded within matrix material layer 30 (that is, without gaps or protrusions out of the inner or outer surface boundary of matrix material layer 30). The term "embedded" is used herein to describe both partially embedding and fully embedding braided mesh assembly 28 within matrix material layer 30. This is depicted in FIG. 5 as plait matrix layer 40.

As described above, plait matrix layer 40 is hyperelastic relative to at least one of inner layer 26 and outer layer 32 as a result of the use of matrix material layer 30. This hyperelasticity permits braided mesh assembly 28 to adjust its deformed conformations by introducing relatively large localized material strains (e.g., localized opening and closing of the braid plaits) within plait matrix layer 40 with a reduced risk of concomitant material failure (e.g., material yielding and tearing). Similar strain adjustments will take place at the interphase of plait matrix layer 40 and inner layer 26 and the interphase of plait matrix layer 40 and outer layer 32 when catheter shaft 12 is subjected to bending, flexing, tension, compression, or any combination of such loads. Thus, a catheter shaft according to the present invention exhibits improved mechanical integrity even if the load exceeds the yield strain of either or both of inner layer 26 and outer layer 32. Moreover, the hyperelasticity of plait matrix layer 40 will tend to "drive" braided mesh assembly 28 to "quasi-elastically" recover its undeformed conformation, even if the load exceeds the yield strain of either or both of inner layer 26 and outer layer 32. In sum, the hyperelasticity of plait matrix layer 40, along with its lessened constraints upon braided mesh assembly 28, improve the kink resistance and mechanical integrity of a catheter shaft constructed according to the present invention.

As described above, the plaits within braided wire mesh assembly 28 may adjust their conformations as catheter shaft 12 is maneuvered (e.g., pushed, torqued, and flexed), thereby introducing localized strain redistributions inside plait matrix layer 40. Therefore, it is contemplated that braided wire mesh assembly 28 may be coated, for example with silicone, to form thin polymeric films on braided wire mesh assembly 28 and facilitate the spring-like hyperelastic recovery performance of plait matrix layer 40 as described above.

In one exemplary embodiment of the invention, both inner layer 26 and outer layer 30 are formed of Pebax® 7233 filled with 40% barium sulfate fillers and matrix material layer 30 is formed of Pebax® 4033.

In another exemplary embodiment of the invention, one of inner layer 26 and outer layer 30 is formed of Pebax® 6333 filled with 40% barium sulfate fillers and the other of inner layer 26 and outer layer 30 is formed of Pebax® 7233 filled with 40% barium sulfate fillers. Matrix layer 30 is formed of Pebax® 4033.

In yet another exemplary embodiment of the invention, inner layer 26 is formed of Makrolon 1239, matrix layer 30 is formed of Pebax® 4033, and outer layer 32 is formed of Pebax® 6333 filled with 40% barium sulfate fillers. Alternatively, outer layer 32 may be formed of Pebax® 7233 filled with 40% barium sulfate fillers.

In a further exemplary embodiment of the invention, inner layer 26 is formed of Makrolon 1239, matrix layer 30 is formed of Surlyn 9320, and outer layer 32 is formed of Pebax® 7233 filled with 40% barium sulfate fillers.

Although several embodiments of this invention have been described above with a certain degree of particularity, those skilled in the art could make numerous alterations to the disclosed embodiments without departing from the spirit or scope of this invention. For example, a catheter formed according to the present invention may have varying sizes and varying uses, including, but not limited to, the treatment of atrial fibrillation and the treatment of atrial tachycardia.

One of ordinary skill in the art will also appreciate that other modifications could be made to the catheter shaft assembly herein without departing from the spirit and scope of the present invention. For example, the catheter shaft assembly could be made steerable, for example as described in U.S. application Ser. No. 11/647,313, filed 29 Dec. 2006 ("the '313 application"), or with embedded internal components, for example as described in U.S. application Ser. No. 11/646,578, filed 28 Dec. 2006 ("the '578 application"). Both the '313 application and the '578 application are hereby incorporated by reference as though fully set forth herein.

In addition, it is contemplated that a catheter according to the present invention may be manufactured using alternative techniques. For example, rather than bonding the layers of the catheter shaft assembly via melt-processing (e.g., reflow bonding) as generally described above, one or more layers may be extruded over one another (e.g., extrusion of matrix material layer 30 over braided mesh assembly 28). Where one or more layers are extruded, they may be coextruded (e.g., coextrusion of matrix material layer 30 and outer layer 32). Of course, it is also within the spirit and scope of the invention to utilize a combination of reflow bonding and extrusion processes (e.g., reflow bonding matrix material layer 30, braided mesh assembly 28, and inner layer 26, followed by extrusion of outer layer 32 thereabout). As another example, the various polymeric layers may be formed by wrapping or winding a suitable material about the catheter shaft assembly (e.g., wrapping surface-etched PTFE tape about mandrel 24 to form inner layer 26).

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of manufacturing a catheter shaft, comprising:
   forming a plait matrix layer, the plait matrix layer including a braided wire mesh embedded in a first material; and
   forming an outer layer of a second material about the plait matrix layer and extending continuously along a length of the plait matrix layer,
   wherein the first material has a lower flexural modulus and a higher yield strain than the second material.

2. The method according to claim 1, wherein the first material comprises a melt-processable polymer.

3. The method according to claim 1, wherein the second material comprises a melt-processable polymer.

4. The method according to claim 1, wherein at least one of the first material and the second material comprises a particulate radiopaque filler material.

5. The method according to claim 1, wherein the step of forming a plait matrix layer comprises:
   braiding the wire mesh to form a reinforced layer; and
   extruding the first material about the reinforced layer to form the plait matrix layer.

6. The method according to claim 1, further comprising heating the plait matrix layer and the outer layer to bond the outer layer to the plait matrix layer.

7. The method according to claim 6, further comprising introducing a heat-shrink tube adjacent the outer layer prior to the heating step.

8. The method according to claim 1, wherein the outer layer extends continuously along an entire length of the plait matrix layer.

* * * * *